United States Patent [19]
Clawson et al.

[11] Patent Number: 5,834,657
[45] Date of Patent: Nov. 10, 1998

[54] APPARATUS AND METHODS FOR SENSING FLUID PARAMETERS

[75] Inventors: Allen Dale Clawson, San Luis Obispo; Fredrick Salter, Arroyo Grande, both of Calif.

[73] Assignee: Del Industries Inc., San Luis Obispo, Calif.

[21] Appl. No.: 766,006

[22] Filed: Dec. 13, 1996

[51] Int. Cl.⁶ ................................................... G01N 1/10
[52] U.S. Cl. .................................. 73/863.81; 73/863.51; 73/863.61
[58] Field of Search .......................... 73/863.61, 863.58, 73/866.5, 863.51, 863.81, 864.81; 374/208, 209, 210

[56] References Cited

U.S. PATENT DOCUMENTS

| | | | |
|---|---|---|---|
| 2,481,882 | 9/1949 | Sebald et al. ......................... | 73/863.61 |
| 3,007,340 | 11/1961 | Kraftson ................................ | 73/866.5 |
| 3,765,226 | 10/1973 | Strickland et al. ................... | 73/863.61 |
| 3,803,921 | 4/1974 | Dieterich .............................. | 73/863.61 |
| 4,353,260 | 10/1982 | Round .................................. | 73/861.61 |
| 5,625,156 | 4/1997 | Serrels et al. ........................ | 73/863.51 |

*Primary Examiner*—Ronald L. Biegel
*Attorney, Agent, or Firm*—Frank J. Uxa

[57] ABSTRACT

Apparatus to facilitate sensing a parameter of a fluid in a conduit include a tap body including a first end region and a second end region. The tap body is adapted to be secured to the wall of a conduit so that the first end region extends into the conduit and the second end region extends outside of the conduit. The tap body defines a fluid flow passage which includes an inlet located in the first end region, an inlet leg in fluid communication with the inlet, a sample zone at least partially in the second end region and in fluid communication with the inlet leg, an outlet leg in fluid communication with the sample zone and an outlet located in the first end region and in fluid communication with the outlet leg. The tap body is further adapted to be secured to a sensor device including a sensor effective in sensing at least one parameter of fluid in the sample zone. Methods for sensing a parameter of a fluid in a conduit are also provided.

18 Claims, 2 Drawing Sheets

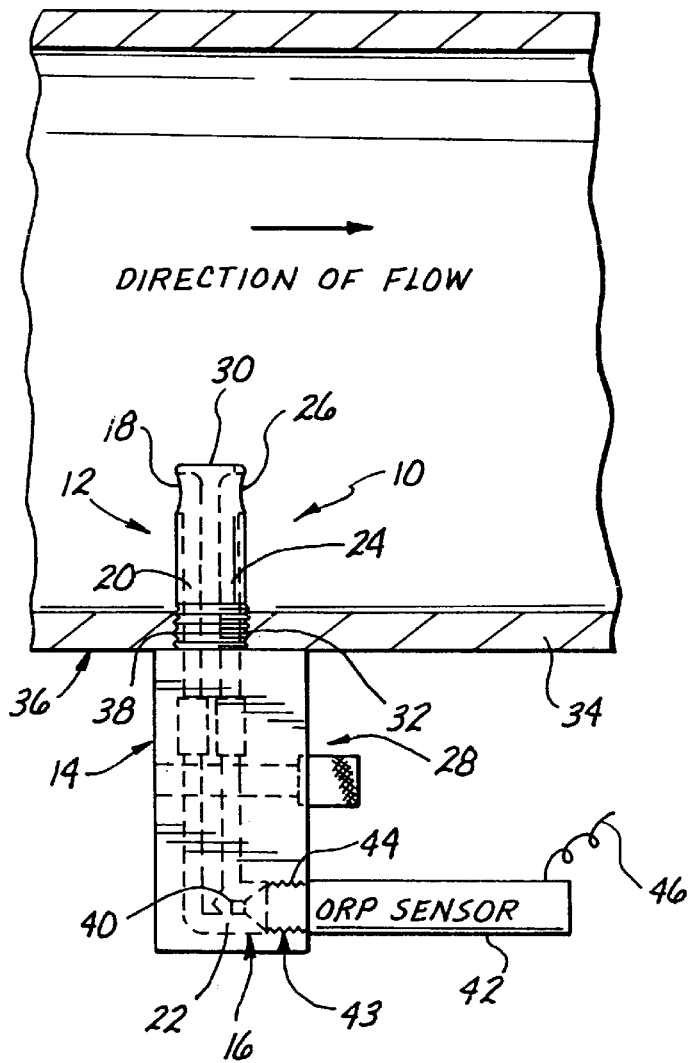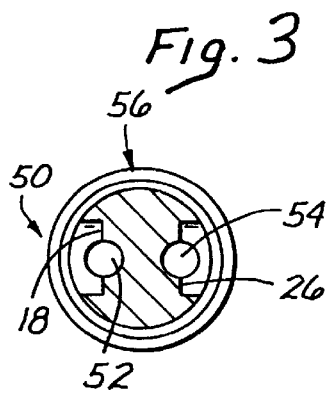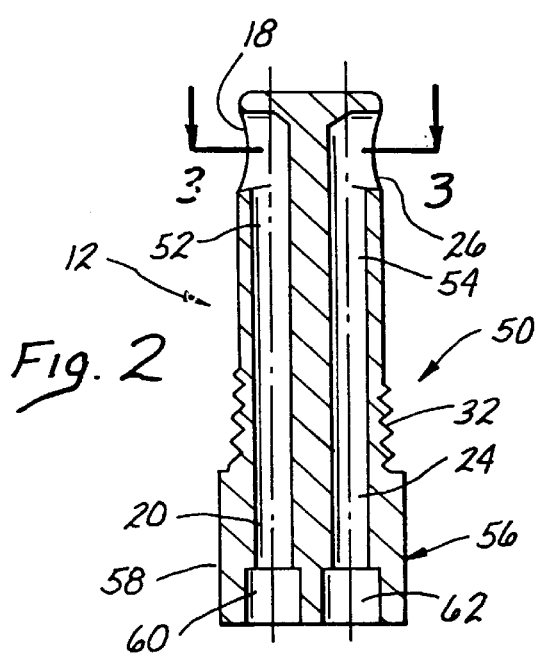

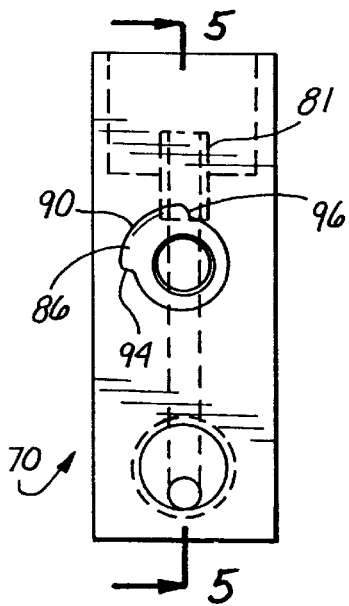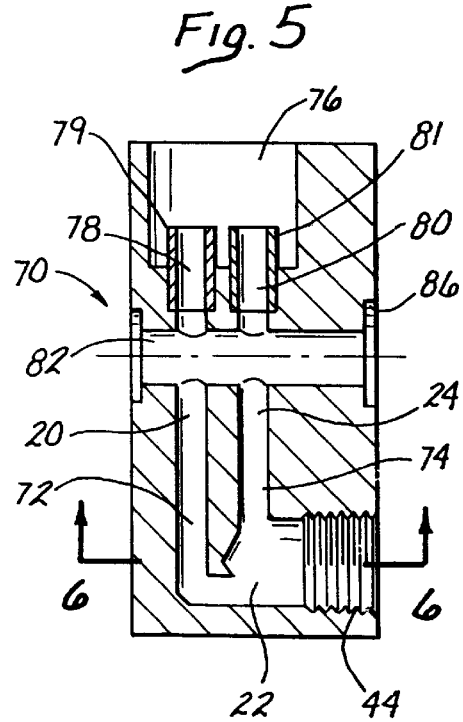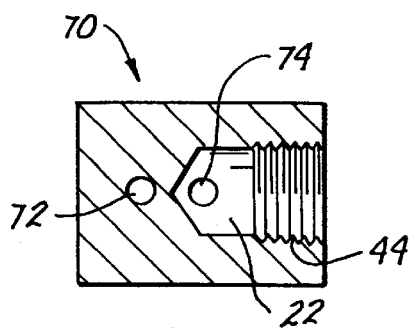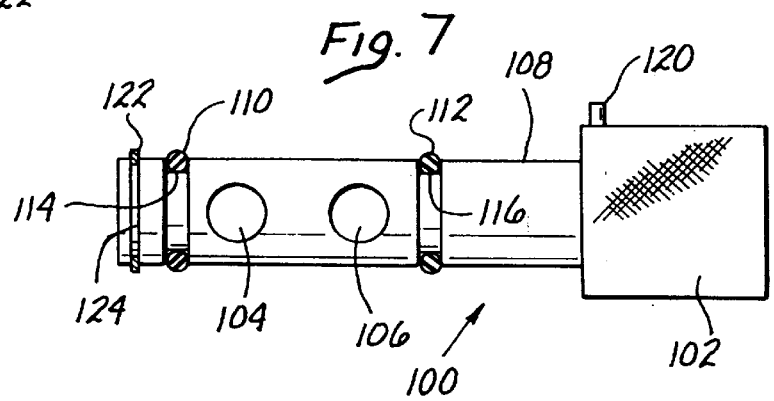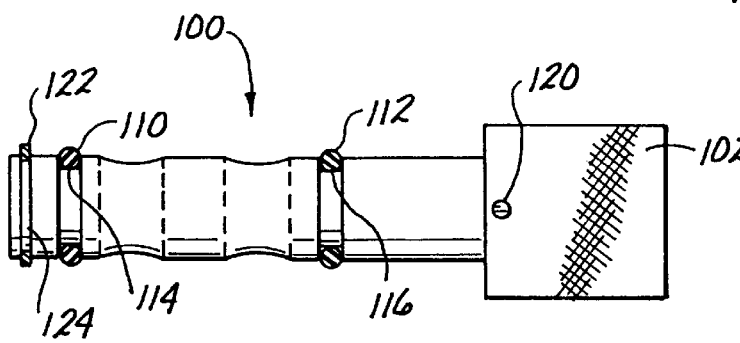

APPARATUS AND METHODS FOR SENSING FLUID PARAMETERS

BACKGROUND OF THE INVENTION

The present invention is related to apparatus and methods to facilitate sensing one or more parameters of a fluid contained in a conduit. More particularly, the invention relates to apparatus and methods to facilitate sensing one or more parameters in a fluid flowing through a conduit such that the sensor is located spaced apart from the conduit.

It is often advantageous to sense or measure one or more parameters, e.g., oxidation reduction potential (ORP), temperature, pH, one or more compositional parameters, other properties and the like, of a fluid, for example, a liquid stream, flowing through a conduit. Conventionally, the sensor or sensor probe is mounted on the conduit, for example, piping which can be 10 inches or larger in diameter, so that the sensor/probe extends directly into the conduit. However, periodic cleaning of the sensor/probe is necessary for proper operation. With the sensor/probe mounted directly in the conduit, the fluid flow often has to be turned off in order to remove the sensor/probe without substantial spillage. This can result in extended and costly process downtime. Alternately, removal of the sensor/probe with fluid continuing to flow in the conduit results in spillage of the fluid which is at least inconvenient and can be harmful or even dangerous.

Sophisticated, relatively complex and expensive "hot tap" devices are available which involve a compression nut and an isolation ball valve to remove the sensor/probe without shutdown. However, many problems exist with these devices. Another approach involves installing bypass or sample lines. However, this approach is somewhat extravagant and can result in significant additional costs.

It would be advantageous to provide straightforward apparatus and methods effective to facilitate sensing a parameter of a fluid in a conduit.

SUMMARY OF THE INVENTION

New apparatus and methods effective to facilitate sensing at least one parameter of a fluid in a conduit have been discovered. The present apparatus are straightforward in construction, and easy to produce and use. The present apparatus install at a single point, for example, in a tapped hole or a T in the wall of a conduit, particularly a conduit which is 3 inches in diameter (inside) or larger. The present apparatus provide for fluid flow from the conduit into the apparatus and then back into the conduit, preferably with no external power being employed. The present systems provide isolation of the sensor/probe for regular maintenance, removal and/or replacement, as necessary. This maintenance/replacement is achieved without disrupting the flow of fluid in the conduit and without resulting in significant leakage of the fluid from the conduit. The present apparatus can be configured to be in close proximity to the conduit, rather than having long protrusions or extensions from the conduit, such as in many bypass or sample line systems. For example, the entire apparatus preferably extends no more than about 4 to about 6 inches from the outside of the conduit wall.

In one broad aspect of the present invention, apparatus to facilitate sensing at least one parameter of a fluid, preferably a liquid, in a conduit are provided. Such apparatus comprises a tap body having a first end region and a second end region. The tap body is adapted to be secured to the wall of a conduit so that the first end region extends into the conduit and the second end region extends outside the conduit. The tap body defines a fluid flow passage which includes an inlet located in the first end region, an inlet leg in fluid communication with the inlet, a sample zone at least partially in the second end region and in fluid communication with the inlet leg, an outlet leg in fluid communication with the sample zone, and an outlet located in the first end region and in fluid communication with the outlet leg. The tap body is further adapted to be secured to a sensor device, for example, a probe, including a sensor effective in sensing at least one parameter of fluid in the sample zone.

The fluid flow passage is preferably adapted so that a portion of the fluid in the conduit passes into, through and out of the fluid flow passage. More preferably, this flow of fluid into, through and out of the fluid flow passage occurs without any additional activation force, for example, mechanical or other pumping force, other than the force of the fluid flowing in the conduit.

The inlet and outlet preferably face in substantially opposing directions. More preferably, the inlet is situated to be upstream of the outlet in the conduit and, still more preferably, oriented substantially perpendicular to the general direction of fluid flow in the conduit. The tap body preferably includes a first end and each of the inlet and the outlet is an equal distance from the first end.

The tap body, in one embodiment, includes an outer surface which is threaded to facilitate securing the apparatus to the conduit. The tap body preferably includes a threaded surface effective to facilitate securing the tap body to the sensor device, for example, to seal the sample zone so that fluid flows from the sample zone substantially only through the fluid flow passage of the apparatus.

In a particularly useful embodiment, the tap body comprises a tap stem which includes the first end region, the inlet, the outlet, a portion of the inlet leg and a portion of the outlet leg. A flow cell body, preferably coupled to the tap stem, is provided and includes a portion of the inlet leg, a portion of the outlet leg, the sample zone and the second end region. The flow cell body preferably defines a cavity and a portion of the tap stem is located in this cavity. More preferably, this portion of the tap stem is adhesively held in the cavity, for example, such as by a combination of interference fitting the tap stem into the cavity and the use of an adhesive component.

The apparatus preferably further comprises a valve element adapted to cooperate with the tap body. The valve element is adapted or configured to be placed in a first position so that the fluid flow passage is open and in a second position such that the fluid flow passage is substantially closed. The valve element is preferably such that it can very effectively be manually turned between the first position and the second position. In one embodiment, the valve element is preferably adapted to intersect both the inlet leg and the outlet leg to substantially prevent fluid flow in both the inlet leg and the outlet leg. The valve element preferably includes one or more sealing members, for example, O-rings, positioned and effective to substantially prevent fluid flowing in the inlet leg and outlet leg from leaking from the apparatus.

In a very useful embodiment, the tap body includes an indent and the valve element includes a turning knob sized and adapted to partially fit in this indent. Preferably, the indent and turning knob are configured to limit the degree to which the valve element can be turned. This feature is also very useful in providing a visual indication of whether the valve element is in the first or second position.

In another broad aspect of the present invention, methods for sensing at least one parameter of a fluid in a conduit, preferably of fluid flowing in a conduit, are provided. These methods comprise a causing step and a sensing step and are preferably practiced using the apparatus described herein.

A quantity of fluid, for example, liquid such as liquid water or another liquid aqueous medium, in a conduit is caused to pass through a fluid flow passage, for example, as described elsewhere herein. This fluid flow passage includes an inlet located in the conduit, an inlet leg in fluid communication with the inlet, a sample zone at least partially located outside the conduit and in fluid communication with the inlet leg, an outlet leg extending into the conduit and in fluid communication with the sample zone and an outlet located in the conduit and in fluid communication with the outlet leg. A parameter of the quantity of fluid is sensed with a sensor in the sample zone.

The inlet is advantageously located upstream relative to the outlet. Such orientation causes flow to be developed through the fluid flow passage, for example, by taking advantage of the kinetic pressure of the fluid flowing in the conduit. By placing the portion of the apparatus including the inlet in the conduit in which fluid is flowing, an area on the upstream face of this portion of the apparatus is at an increased pressure (higher than the fluid pressure in the conduit) proportional to the velocity of the fluid flowing in the conduit. This effect is believed to provide the driving force for the flow of fluid through the fluid flow passage. This flow producing effect is enhanced, or even maximized, with the inlet facing directly into (perpendicular to) the direction of fluid flowing in the conduit and the outlet facing directly opposite the direction of fluid flowing in the conduit. With the outlet thus oriented, the outlet is exposed, for example, because of eddy effects, to a reduced or decreased pressure (lower than the fluid pressure in the conduit) which additionally facilitates the flow of fluid through the fluid flow passage.

In one useful embodiment, the methods preferably further comprise sealing the sample zone to prevent fluid leaving the sample zone other than through the above-noted fluid flow passage.

The flow of fluid through the fluid flow passage preferably can be substantially prevented, as desired. For example, a valving arrangement, such as described elsewhere herein, can be employed to substantially prevent the flow of fluid through the fluid flow passage. More preferably, the present methods further comprise removing the sensor from the sample zone; thereafter, placing the sensor or a replacement sensor in the sample zone while fluid flow in the fluid flow passage is being substantially prevented; and, thereafter, repeating the causing step and the sensing step, as described herein. In this embodiment, the sensor can be very easily, effectively and conveniently cleaned or replaced without causing a process shutdown and without causing any significant fluid spillage.

These and other aspects of the present invention will be apparent in the following detailed description and claims, particularly when considered in conjunction with the accompanying drawings in which like parts bear like reference numerals.

BRIEF DESCRIPTION OF THE DRAWINGS

FIG. 1 is a somewhat schematic illustration showing an apparatus in accordance with the present invention in use.

FIG. 2 is a cross-sectional view of the tap stem of the apparatus in accordance with the present invention shown in FIG. 1.

FIG. 3 is a cross-sectional view taken generally along line 3—3 of FIG. 2.

FIG. 4 is a side plan view of the flow cell body of the apparatus in accordance with the present invention shown in FIG. 1.

FIG. 5 is a cross-sectional view taken generally along line 5—5 of FIG. 4.

FIG. 6 is a cross-sectional view taken generally along line 6—6 of FIG. 5.

FIG. 7 is a side plan view of the valve element of the apparatus in accordance with the present invention shown in FIG. 1.

FIG. 8 is a side plan view of the valve element of the apparatus in accordance with the present invention shown in FIG. 1 rotated through an angle of about 90° relative to the valve element shown in FIG. 7

DETAILED DESCRIPTION OF THE PREFERRED EMBODIMENT

Referring now to the drawings, and in particular to FIG. 1, the present apparatus, shown generally at 10, includes a first end region 12 and a second end region 14. A fluid flow passageway 16 includes an inlet 18, a hollow inlet leg 20, a hollow sample zone 22, a hollow outlet leg 24 and an outlet 26. A valve element, shown generally at 28, is located between the first end region 12 and the second end region 14. As is discussed hereinafter, apparatus 10 facilitates sensing a parameter, for example, the oxidation reduction potential (ORP), of a liquid. This liquid may be of any useful composition. The liquid can be aqueous-based, for example, drinking or tap water, swimming pool water and the like, or can be non-aqueous-based, for example, hydrocarbons and the like. In addition, the apparatus 10 can be employed to facilitate monitoring or sensing a parameter of a gaseous material.

As shown in FIG. 1 with the general direction of liquid flow being from left to right, inlet 18 is located upstream relative to outlet 26. Also, both inlet 18 and outlet 26 are located an equal distance below top 30 of apparatus 10.

Apparatus 10 includes an outer surface 32 which is threaded to facilitate securing apparatus 10 to the wall 34 of conduit 36 through a hole in wall 34 defined by threads 38. An operational sensor, for example, an ORP sensor 40, is secured to a probe 42 and extends into the sample zone 22. The probe 42 includes a threaded surface 43 which matingly engages a threaded surface 44 in the second end region 14. This allows the probe 42 to be sealingly secured to the apparatus 10. Signals from sensor 40, indicative of the ORP of the liquid in sample zone 42, are transmitted through sensor cable 46 to a conventional display device, such as a printer and/or video monitor, (not shown) where the ORP of the liquid in sample zone 22 is monitored.

Each of the individual components of apparatus 10 are described below in substantial detail. The components of apparatus 10 are made from any suitable material or materials of construction. Apparatus 10 should be made of materials which are substantially unaffected by the liquid in conduit 36, by the conditions at which conduit 36 is operated and by the operation of the apparatus itself. Of course, the apparatus 10 should have no significant harmful effect on the liquid in conduit 36 or in the operation of the conduit. When aqueous-based liquids are involved, apparatus 10 is made, for the most part, out of materials selected from metals, polymeric materials and combinations thereof. The material or materials of construction of apparatus 10 are preferably compatible with the material of construction of conduit 36, for example, so that no corrosion or other detrimental interaction between apparatus 10 and conduit 36 occurs.

In FIGS. 2 and 3, tap stem 50 is shown. Tap stem 50 includes first end region 12, threaded outer surface 32, inlet 18, outlet 26 and first portion 52 of inlet leg 20 and second portion 54 of outlet leg 24. First portion 52 and second portion 54 are mutually parallel.

The proximal end 56 includes an outer peripheral surface 58 which is somewhat enlarged. In addition, the inlet leg 20 includes a somewhat enlarged portion 60 at the proximal end 56. Similarly, the outlet leg 24 includes a somewhat enlarged portion 62 located at the proximal end 56 of tap stem 50. The threaded outer surface 32 is located on tap stem 50 distally of proximal end 56. In use, proximal end 50 is located outside of conduit 36.

Referring now to FIGS. 4, 5 and 6, flow cell body 70 includes a second portion 72 of the inlet leg 20 and a first portion 74 of the outlet leg 24. Second portion 72 of inlet leg 20 leads directly into the sample zone 22 which is defined by flow cell body 70. First portion 74 of outlet leg 22 is in direct fluid communication with sample zone 22 so that liquid from sample zone 22 can flow through the first portion 74 as it leaves the sample zone. Flow cell body 70 includes threaded surface 44 which is adapted to be mated with threaded surface 43 on sensor probe 42 so as to secure the sensor probe to flow cell body 70 with the ORP sensor 40 located in the sample zone 22.

Sample zone 22 is configured, adapted and situated so that liquid from inlet leg 20 is directed at ORP sensor 40. For example, sample zone 22 is configured so that ORP sensor 40 can be positioned directly in the path of the fluid as it flows through the sample zone. Also, the cross-section of sample zone 22 is somewhat enlarged relative to the cross-sections of inlet leg 20 and outlet leg 24. This, together with locating the sample zone at or near the bottom of the fluid flow passage, facilitates advantageous intimate contacting between the liquid and ORP sensor 40. In short, the sample zone 22 is constructed to enhance the ability of ORP sensor 40 to accurately sense the ORP of the liquid in the conduit even though the flow of liquid through the fluid flow passage is relatively small.

Flow cell body 70 includes a cavity 76 which is sized and adapted to receive a substantial portion of the enlarged region 56 of tap stem 50. This enlarged region 56 is held in the cavity 76 of flow cell body 70 using a combination of interference fitting and an adhesive or glue component.

Flow cell body 70 includes a somewhat enlarged portion 78 of inlet leg 20 and a somewhat enlarged portion 80 of outlet leg 24. Bushing inserts 79 and 81 are interference fitted into enlarged portions 78 and 80, respectively. Bushing inserts 79 and 81 have the same outside diameters as the inside diameters of enlarged portions 78 and 80, respectively, and the inside diameters of enlarged portions 60 and 62, respectively. Bushing inserts 79 and 81 extend beyond enlarged portions 78 and 80, respectively. When the tap stem 12 and flow cell body are assembled, the bushing inserts 79 and 81 extend into enlarged portions 60 and 62, respectively, so as to butt up against end walls 61 and 63, respectively.

With the bushing inserts 79 and 81 in place in enlarged portions 78 and 80, respectively, adhesive is applied to the walls of cavity 76 and enlarged region 56. The enlarged region 56 is placed into the cavity 76 so that bushing insert 76 extends into enlarged portion 60 and bushing insert 81 extends into enlarged portion 62. Thus, bushing inserts 79 and 81 facilitate assembling apparatus 10 so that first portion 52 of inlet leg 20 is properly joined to second portion 72 of the inlet leg and first portion 74 of outlet leg 24 is properly joined to second portion 54 of the outlet leg. In addition, the bushing inserts 79 and 81 are effective in preventing adhesive from blocking or otherwise obstructing the inlet leg 20 and outlet leg 24, respectively. Also, the bushing inserts 79 and 81 act to strengthen the coupling or bond between the tap stem 12 and flow cell body 70. Such strengthening is often important, for example, since the tap stem 12 may be threaded into conduit 36 by turning the flow cell body 70 of apparatus 10.

In addition, flow cell body 70 includes a through hole 82 which intersects both inlet leg 20 and outlet leg 24. Flow cell body 70 further includes a shouldered indent 86 which surrounds one end of hole 82 and extends inwardly from the outer surface 88 of the flow cell body. Shouldered indent 86 includes a 90° segment 90 which is somewhat enlarged from the remainder of shouldered indent 86. This enlarged segment 90 extends from first shoulder 94 to second shoulder 96.

Although tap stem 50 and flow cell body 70 are illustrated as separate components, a single integral component providing the desired features described herein can be molded, cast, machined or otherwise provided and used in place of this two component assembly.

Referring now to FIGS. 7 and 8, a valve element, shown generally at 100, includes a turning knob 102, an inlet through hole 104 and an outlet through hole 106. These through holes 104 and 106 are located in valve stem 108 which is sized and adapted to be received in through hole 82 of flow cell body 70. Through hole 104 can be considered a part of inlet leg 20, while through hole 106 can be considered a part of outlet leg 24. O-ring seals 110 and 112 are held in grooves 114 and 116 in valve stem 108. These O-ring seals 110 and 112 substantially prevent liquid passing through inlet leg 20 and outlet leg 24 from leaking from apparatus 10.

With valve element 100 in place in through hole 82, turning knob 102 extends into shouldered indent 86 so that index pin 120 on the turning knob is free to rotate through a 90° rotation between shoulders 94 and 96. Valve element 100 is held in through hole 82 by placing a lock ring 122 in outwardly extending lock groove 124 on valve stem 108 after the valve element is passed into the through hole. Valve element 100 can be removed from through hole 82 by first removing lock ring 122 from lock groove 124.

The function of valve element 100 is to allow liquid to flow freely in inlet leg 20, sample zone 22 and outlet leg 24, as desired, and to substantially prevent such fluid flow, as desired. By manually turning the turning knob 102 to a first position in which the pin 120 is located in contact with shoulder 94, liquid is allowed to flow through inlet leg 20 and outlet leg 24. By turning the turning knob 102 a quarter of a rotation so that the pin 120 is in contact with shoulder 96, the flow of liquid through the inlet leg 20 and outlet leg 24 is substantially prevented.

Apparatus 10 functions as follows. After assembly and placement into the threaded hole 38 of conduit 36, apparatus 10 is ready for use.

With the valve element 100 positioned to prevent flow of liquid through inlet leg 20 and outlet leg 24, probe 42 is threaded onto apparatus 10 so that ORP sensor 40 is located in sample zone 22. When it is desired to measure the ORP of the liquid in conduit 36, the valve element 100 is rotated 90° so that liquid from conduit 36 flows into inlet 18, inlet leg 20, sample zone 22, outlet leg 24 and outlet 26 back into the conduit 36. When this flow is established, the ORP sensor 40 is effective in providing signals which are indicative of the ORP of the liquid in sample zone 22. The liquid in sample zone 22 of course has the same composition, and ORP, as the liquid in conduit 36. These signals are passed by cable 46 to a conventional ORP display device, not shown. The ORP of the liquid in sample zone 22 can be monitored continuously by allowing liquid to flow continuously as noted above. Alternately, the ORP of the liquid in the sample zone 22 can be determined periodically. In this later situation, it may be advantageous to turn the valve element 100 so as to prevent flow of liquid through inlet leg 20 and outlet leg 24 when the ORP is not being sensed.

In addition, when it is desired to perform maintenance on sensor 40 or to replace sensor 40, valve element 100 is turned so as to substantially prevent fluid from flowing through inlet leg 20 and outlet leg 24. The probe 42 is then unthreaded from the apparatus 10 to facilitate maintenance on or replacement of sensor 40. Once this maintenance or replacement has occurred, the probe 42 is again threaded into apparatus 10 so that the sensor 40 is located in sample zone 22. Valve element 100 is then turned to allow liquid flow in inlet leg 20 and outlet leg 24. The ORP of the liquid in sample zone 22 is again continuously or periodically determined.

More than one parameter may be sensed or monitored using the present system. For example, more than one sensor can be placed in sample zone 22. Alternately, a number of apparatus, each similar to apparatus 10, can be used with different sensors can be deployed at different locations along the length of conduit 36 to sense or monitor different parameters of the liquid in the conduit. Still further, the apparatus 10 can have more than one opening to sample zone 22 so that a plurality of sensor probes and associated sensors can be used to sense or monitor a plurality of parameters of liquid in conduit 36.

The present apparatus provides a very straightforward, effective, reliable and convenient approach to sensing and/or monitoring at least one parameter of a fluid in a conduit. The present system minimizes fluid spillage, while facilitating parameter sensing or monitoring accuracy, for example, since the sensors can be subjected to maintenance and/or replaced very easily and conveniently.

While this invention has been described with respect to various specific examples and embodiments, it is to be understood that the invention is not limited thereto and that it can be variously practiced within the scope of the following claims.

What is claimed is:

1. An apparatus to facilitate using a sensor device in sensing at least one parameter of a fluid in a conduit, said apparatus comprises:

a tap body having a first end region and a second end region and adapted to be secured to the wall of a conduit so that said first end region extends into said conduit and said second end region extends outside of said conduit;

said tap body defining a fluid flow passage which includes an inlet located in said first end region, an elongated inlet leg in fluid communication with said inlet, a sample zone at least partially in said second end region and in fluid communication with said inlet leg, an elongated outlet leg in fluid communication with said sample zone and an outlet located in said first end region and in fluid communication with said outlet leg, said inlet leg and said outlet leg being of differing lengths;

said tap body being further adapted to be secured to the sensor device effective in sensing at least one parameter of fluid in said sample zone; and said tap body comprises a tap stem which includes said first end region, said inlet, said outlet, a portion of said inlet leg and a portion of said outlet leg; and a flow cell body which includes a portion of said inlet leg, a portion of said outlet leg, said sample zone and said second end region.

2. The apparatus of claim 1 wherein said inlet and said outlet face substantially opposing directions.

3. The apparatus of claim 1 wherein said tap body includes a first end and each of said inlet and said outlet is an equal distance from said first end.

4. The apparatus of claim 1 wherein said tap body includes a threaded surface effective to facilitate securing said tap body to the sensor device.

5. The apparatus of claim 1 wherein said flow cell body defines a cavity and a portion of said tap stem is located in said cavity.

6. The apparatus of claim 5 wherein said portion of said tap stem is adhesively held in said cavity.

7. The apparatus of claim 1 wherein said inlet leg is longer than said outlet leg.

8. A method of sensing at least one parameter of a fluid in a conduit which comprises:

causing a quantity of fluid in a conduit to pass through a fluid flow passage including an inlet located in said conduit, an elongated inlet leg in fluid communication with said inlet, a sample zone in fluid communication with said inlet leg and located at least partially outside said conduit, an elongated outlet leg in fluid communication with said sample zone and extending into said conduit, said inlet leg is longer than said outlet leg and an outlet in fluid communication with said outlet leg and located in said conduit, said inlet leg including a sample zone inlet passage opening directly into said sample zone and said outlet leg including a sample zone outlet passage opening directly into said sample zone, and said sample zone inlet passage is oriented at an angle of about 90° relative to said sample zone outlet passage; and sensing a parameter of said quantity of fluid with a sensor located in said sample zone.

9. The method of claim 8 which further comprises substantially preventing the flow of fluid through said fluid flow passageway, as desired.

10. The method of claim 9 which further comprises removing said sensor from said sample zone while substantially preventing the flow of fluid through said fluid flow passageway; thereafter placing said sensor or a replacement sensor in said sample zone; and, thereafter, repeating said causing step and said sensing step.

11. An apparatus to facilitate using a sensor device in sensing at least one parameter of a fluid in a conduit, said apparatus comprises:

a tap body having a first end region and a second end region and adapted to be secured to the wall of a conduit so that said first end region extends into said conduit and said second end region extends outside of said conduit;

said tap body defining a fluid flow passage which includes an inlet located in said first end region, an inlet leg in fluid communication with said inlet, a sample zone at least partially in said second end region and in fluid communication with said inlet leg, an outlet leg in fluid communication with said sample zone and an outlet located in said first end region and in fluid communication with said outlet leg;

said tap body being further adapted to be secured to the sensor device effective in sensing at least one parameter of fluid in said sample zone;

said tap body comprises a tap stem which includes said first end region, said inlet, said outlet, a portion of said inlet leg and a portion of said outlet leg; and a separate flow cell body which is secured to said tap stem and includes a portion of said inlet leg, a portion of said outlet leg, said sample zone and said second end region; and said inlet leg includes a sample zone inlet passage opening directly into said sample zone and said outlet leg includes a sample zone outlet passage opening directly into said sample zone, and said sample zone inlet passage is oriented at an angle of about 90° relative to said sample zone outlet passage.

12. The apparatus of claim 11 wherein said inlet leg is longer than said outlet leg.

13. The apparatus of claim 11 which further comprises a valve element adapted to cooperate with said tap body, and to be placed in a first position such that said fluid flow passage is open and in a second position such that said fluid flow passage in substantially closed, said valve element including a portion located between said inlet leg and said outlet leg having a uniform peripheral dimension.

14. An apparatus to facilitate using a sensor device in sensing at least one parameter of a fluid in a conduit, said apparatus comprises:

a tap body having a first end region and a second end region and adapted to be secured to the wall of a conduit so that said first end region extends into said conduit and said second end region extends outside of said conduit;

said tap body defining a fluid flow passage which includes an inlet located in said first end region, an elongated inlet leg in fluid communication with said inlet, a sample zone at least partially in said second end region and in fluid communication with said inlet leg, an elongated outlet leg in fluid communication with said sample zone and an outlet located in said first end region and in fluid communication with said outlet leg, said inlet leg and said outlet leg being of differing lengths;

said tap body being further adapted to be secured to the sensor device effective in sensing at least one parameter of fluid in said sample zone; and a valve element adapted to cooperate with said tap body, and to be placed in a first position such that said fluid flow passage is open and in a second position such that said fluid flow passage is substantially closed, said valve element including a portion located between said inlet leg and said outlet leg having a uniform peripheral dimension.

15. The apparatus of claim 14 wherein said valve element is adapted to intersect both said inlet leg and said outlet leg to substantially prevent fluid flow in both said inlet leg and said outlet leg.

16. The apparatus of claim 15 wherein said valve element includes O-ring sealing members positioned and effective to substantially prevent fluid flowing in said inlet leg and said outlet leg leaking from said apparatus.

17. The apparatus of claim 14 wherein said tap body includes an indent and said valve element includes a turning knob sized and adapted to partially fit into said indent, said indent and said turning knob being configured to limit the degree to which said valve element can be turned.

18. An apparatus to facilitate using a sensor device in sensing at least one parameter of a fluid in a conduit, said apparatus comprises:

a tap body having a first end region and a second end region and adapted to be secured to the wall of a conduit so that said first end region extends into said conduit and said second end region extends outside of said conduit;

said tap body defining a fluid flow passage which includes an inlet located in said first end region, an elongated inlet leg in fluid communication with said inlet, a sample zone at least partially in said second end region and in fluid communication with said inlet leg, an elongated outlet leg in fluid communication with said sample zone and an outlet located in said first end region and in fluid communication with said outlet leg, said inlet leg and said outlet leg being of differing lengths;

said tap body being further adapted to be secured to the sensor device effective in sensing at least one parameter of fluid in said sample zone; and said inlet leg includes a sample zone inlet passage opening directly into said sample zone and said outlet leg includes a sample zone outlet passage opening directly into said sample zone, and said sample zone inlet passage is oriented at an angle of about 90° relative to said sample zone outlet passage.

* * * * *